(12) United States Patent
Putzig

(10) Patent No.: US 8,242,060 B2
(45) Date of Patent: Aug. 14, 2012

(54) STABLE SOLUTIONS OF ZIRCONIUM HYDROXYALKYLETHYLENE DIAMINE COMPLEX AND USE IN OIL FIELD APPLICATIONS

(75) Inventor: Donald Edward Putzig, Newark, DE (US)

(73) Assignee: Dorf Ketal Specialty Catalysts, LLC, Stafford, TX (US)

( * ) Notice: Subject to any disclaimer, the term of this patent is extended or adjusted under 35 U.S.C. 154(b) by 576 days.

(21) Appl. No.: 11/643,513

(22) Filed: Dec. 21, 2006

(65) Prior Publication Data

US 2008/0149341 A1 Jun. 26, 2008

(51) Int. Cl.
C23F 11/18 (2006.01)
C23F 11/14 (2006.01)
C09K 8/68 (2006.01)
E21B 43/16 (2006.01)
E21B 43/26 (2006.01)

(52) U.S. Cl. ..... 507/271; 507/211; 507/244; 166/305.1; 166/308; 166/283

(58) Field of Classification Search ............... 507/271, 507/211, 244; 166/305.1, 308, 283
See application file for complete search history.

(56) References Cited

U.S. PATENT DOCUMENTS

| | | |
|---|---|---|
| 2,824,114 A | 2/1958 | Bostwick |
| 2,824,115 A | 2/1958 | Beacham et al. |
| 2,894,966 A * | 7/1959 | Russell ............................ 556/2 |
| 2,978,347 A | 4/1961 | Koehler et al. |
| 3,525,690 A | 8/1970 | Christian |
| 3,888,312 A | 6/1975 | Tiner et al. |
| 4,382,874 A | 5/1983 | Jenkins |
| 4,460,751 A | 7/1984 | Hanlon et al. |
| 4,477,360 A | 10/1984 | Almond |
| 4,488,975 A | 12/1984 | Almond |
| 4,524,829 A | 6/1985 | Hanlon et al. |
| 4,534,870 A | 8/1985 | Williams |
| 4,553,601 A | 11/1985 | Almond et al. |
| 4,578,488 A | 3/1986 | Rummo et al. |
| 4,579,670 A | 4/1986 | Payne |
| 4,657,081 A | 4/1987 | Hodge |
| 4,677,201 A | 6/1987 | Morgan |
| 4,683,068 A | 7/1987 | Kucera |
| 4,686,052 A | 8/1987 | Baranet et al. |
| 4,702,848 A | 10/1987 | Payne |
| 4,749,041 A | 6/1988 | Hodge |
| 4,797,216 A | 1/1989 | Hodge |
| 4,798,902 A * | 1/1989 | Putzig ............................ 556/54 |
| 4,883,605 A | 11/1989 | Putzig |
| 5,165,479 A | 11/1992 | Harris et al. |
| 5,217,632 A | 6/1993 | Sharif |
| 5,271,466 A | 12/1993 | Harms |
| 5,273,580 A | 12/1993 | Totten et al. |
| 5,305,832 A | 4/1994 | Gupta et al. |
| 5,462,683 A | 10/1995 | Kinoshita et al. |
| 5,466,846 A | 11/1995 | Sharif |
| 5,478,802 A | 12/1995 | Moradi-Araghi |
| 5,512,188 A | 4/1996 | Kinoshita et al. |
| 5,547,025 A | 8/1996 | Ahmed et al. |
| 5,558,161 A | 9/1996 | Vitthal et al. |
| 5,569,643 A | 10/1996 | Kinoshita et al. |
| 5,614,475 A | 3/1997 | Moorhouse et al. |
| 5,642,783 A | 7/1997 | Moradi-Araghi et al. |
| 5,650,633 A | 7/1997 | Ahmed et al. |
| 5,688,894 A | 11/1997 | Ridland |
| 5,708,107 A | 1/1998 | Ahmed et al. |
| 5,785,747 A | 7/1998 | Vollmer et al. |
| 5,789,350 A | 8/1998 | Moradi-Araghi et al. |
| 5,789,351 A | 8/1998 | Ahmed et al. |
| 5,798,320 A | 8/1998 | Dawson et al. |
| 5,849,674 A | 12/1998 | Fox et al. |
| 5,883,210 A | 3/1999 | Ahmed et al. |
| 5,922,653 A | 7/1999 | Ahmed et al. |
| 5,950,731 A | 9/1999 | Shuchart et al. |
| 6,051,670 A | 4/2000 | Ahmed et al. |
| 6,186,235 B1 | 2/2001 | Tjon-Joe-Pin et al. |
| 6,214,773 B1 | 4/2001 | Harris et al. |
| 6,333,423 B1 | 12/2001 | Kol et al. |
| 6,387,986 B1 | 5/2002 | Moradi-Araghi et al. |
| 6,454,008 B1 | 9/2002 | Chatterji et al. |
| 6,488,091 B1 | 12/2002 | Weaver et al. |
| 6,613,720 B1 | 9/2003 | Feraud et al. |
| 6,734,146 B2 | 5/2004 | Chatterji et al. |
| 6,737,386 B1 | 5/2004 | Moorhouse et al. |
| 6,793,018 B2 | 9/2004 | Dawson et al. |
| 6,810,959 B1 | 11/2004 | Qu et al. |
| 6,814,145 B2 | 11/2004 | Maberry et al. |
| 6,818,598 B2 | 11/2004 | Maberry et al. |
| 6,918,445 B2 | 7/2005 | Todd et al. |
| 6,971,448 B2 | 12/2005 | Slabaugh et al. |
| 6,983,801 B2 | 1/2006 | Dawson et al. |
| 7,001,872 B2 | 2/2006 | Pyecroft et al. |
| 7,036,590 B2 | 5/2006 | Harris |
| 7,078,370 B2 | 7/2006 | Crews |
| 7,140,438 B2 | 11/2006 | Frost et al. |
| 7,151,076 B2 | 12/2006 | Qu et al. |

(Continued)

FOREIGN PATENT DOCUMENTS

EP 0138522 A2 4/1985

(Continued)

OTHER PUBLICATIONS

BASF, Performance Chemicals, Aug. 23, 2010, 2 pages, BASF SE, available at www2.basf.us/performancechemical/pdfs/Quadrol_Polyol.pdf.

(Continued)

*Primary Examiner* — Ling Choi
*Assistant Examiner* — Aiqun Li
(74) *Attorney, Agent, or Firm* — Conley Rose, P.C.; Rodney B. Carroll

(57) ABSTRACT

A clear, stable, salt-free solution of a 1:1 molar complex of zirconium and N,N,N',N'-tetrakis-(2-hydroxypropyl)ethylene diamine. The solution can be used in a cross-linking composition comprising a cross-linkable organic polymer for oil field applications such as fluid fracturing and plugging permeable zones in subterranean formations.

21 Claims, No Drawings

U.S. PATENT DOCUMENTS

| | | | |
|---|---|---|---|
| 7,165,617 | B2 | 1/2007 | Lord et al. |
| 7,195,065 | B2 | 3/2007 | Kelly et al. |
| 7,276,466 | B2 | 10/2007 | Todd et al. |
| 7,297,665 | B2 | 11/2007 | Harris et al. |
| 7,347,265 | B2 | 3/2008 | Monroe et al. |
| 7,497,278 | B2 | 3/2009 | Schriener et al. |
| 7,547,665 | B2 | 6/2009 | Welton et al. |
| 7,730,952 | B2 | 6/2010 | Putzig |
| 7,732,383 | B2 | 6/2010 | Putzig |
| 7,795,187 | B2 | 9/2010 | Putzig |
| 7,795,188 | B2 | 9/2010 | Putzig |
| 2003/0092584 | A1 | 5/2003 | Crews |
| 2003/0114539 | A1 | 6/2003 | Weaver et al. |
| 2004/0211568 | A1 | 10/2004 | Funkhouser et al. |
| 2004/0238169 | A1 | 12/2004 | Todd et al. |
| 2005/0137094 | A1 | 6/2005 | Weaver et al. |
| 2005/0215425 | A1 | 9/2005 | Clair et al. |
| 2005/0269099 | A1 | 12/2005 | Stegent et al. |
| 2005/0284637 | A1 | 12/2005 | Stegent et al. |
| 2006/0009363 | A1 | 1/2006 | Crews |
| 2006/0030493 | A1 | 2/2006 | Segura |
| 2006/0264334 | A1 | 11/2006 | Gupta et al. |
| 2007/0187098 | A1 | 8/2007 | Putzig |
| 2007/0187102 | A1 | 8/2007 | Putzig |
| 2008/0242563 | A1 | 10/2008 | Putzig |
| 2009/0227479 | A1 | 9/2009 | Putzig |

FOREIGN PATENT DOCUMENTS

| | | |
|---|---|---|
| EP | 0 278 684 A1 | 8/1988 |
| EP | 0449384 A1 | 10/1991 |
| EP | 0558099 B1 | 9/1993 |
| GB | 2 108 122 A | 5/1983 |
| JP | 2000264893 A | 9/2000 |
| WO | 2006010912 A1 | 2/2006 |
| WO | 2007095018 A3 | 8/2007 |
| WO | WO 2007/095018 A2 | 8/2007 |
| WO | WO 2007/095367 A2 | 8/2007 |
| WO | 2008082504 A1 | 7/2008 |
| WO | 2008121357 A1 | 10/2008 |

OTHER PUBLICATIONS

BASF, "Quadrol® specialty polyol," Technical Bulletin, Aug. 2001, 1 page, BASF Corporation, available at www2.basf.us/urethanechemicals/kun_chemicals_case/pdfs/Quadrol.pdf.

Chaberek, et al., "Hydrolytic tendencies of metal chelate compounds. III. Oxometal Ions," Journal of the American Chemical Society, Feb. 5, 1959, vol. 81, pp. 515-519.

Foreign Communication from a related counterpart application—International Search Report and Written Opinion, PCT/US2008/004123, Sep. 12, 2008, 7 pages.

Foreign Communication from a related counterpart application—International Preliminary Report on Patentability, PCT/US2008/004123, Oct. 6, 2009, 5 pages.

Office Action dated Feb. 27, 2009 (21 pages), U.S. Appl. No. 11/731,049, filed Mar. 30, 2007.

Office Action (Final) dated Oct. 7, 2009 (13 pages), U.S. Appl. No. 11/731,049, filed Mar. 30, 2007.

Office Action dated Feb. 5, 2010 (12 pages), U.S. Appl. No. 11/731,049, filed Mar. 30, 2007.

Office Action (Final) dated Oct. 18, 2010 (14 pages), U.S. Appl. No. 11/731,049, filed Mar. 30, 2007.

Zhao, et al., "Zirconium gel water shutoff agent used in single fluid method," Shiyou Daxue Xuebao, Ziran Kexueban, 1996, vol. 20, No. 1, pp. 43-47 plus 1 abstract page, University of Petroleum, Dongying 257062, People's Republic of China.

BASF Technical Bulletin entitled "Quadrol® polyol," 2002, 1 page, BASF Corporation.

Foreign Communication from a related counterpart application—International Search Report, PCT/US2007/025802, Jun. 12, 2008, 5 pages.

Office Action dated Jul. 14, 2009 (17 pages), U.S. Appl. No. 12/074,953, filed Mar. 7, 2008.

Office Action (Final) dated Mar. 11, 2010 (13 pages), U.S. Appl. No. 12/074,953, filed Mar. 7, 2008.

Office Action dated May 16, 2011 (20 pages), U.S. Appl. No. 11/731,049, filed Mar. 30, 2007.

Office Action (Final) dated Oct. 11, 2011 (13 pages), U.S. Appl. No. 11/731,049, filed Mar. 30, 2007.

Notice of Allowance dated Dec. 2, 2011 (26 pages), U.S. Appl. No. 12/074,953, filed Mar. 7, 2008.

Advisory Action dated Dec. 23, 2011 (7 pages), U.S. Appl. No. 11/731,049, filed Mar. 30, 2007.

Office Action dated Jan. 25, 2012 (9 pages), U.S. Appl. No. 11/731,049, filed Mar. 30, 2007.

* cited by examiner

STABLE SOLUTIONS OF ZIRCONIUM HYDROXYALKYLETHYLENE DIAMINE COMPLEX AND USE IN OIL FIELD APPLICATIONS

FIELD OF THE INVENTION

The present invention relates to zirconium chelates and their use in oil field applications such as hydraulic fracturing and plugging of permeable zones.

BACKGROUND OF THE INVENTION

The production of oil and natural gas from an underground well (subterranean formation) can be stimulated by a technique called hydraulic fracturing, in which a viscous fluid composition (fracturing fluid) containing a suspended proppant (e.g., sand, bauxite) is introduced into an oil or gas well via a conduit, such as tubing or casing, at a flow rate and a pressure which create, reopen and/or extend a fracture into the oil- or gas-containing formation. The proppant is carried into the fracture by the fluid composition and prevents closure of the formation after pressure is released. Leak-off of the fluid composition into the formation is limited by the fluid viscosity of the composition. Fluid viscosity also permits suspension of the proppant in the composition during the fracturing operation. Cross-linking agents, such as borates, titanates or zirconates are usually incorporated into the fluid composition to control viscosity.

Typically, less than one third of available oil is extracted from a well after it has been fractured before production rates decrease to a point at which recovery becomes uneconomical. Enhanced recovery of oil from such subterranean formations frequently involves attempting to displace the remaining crude oil with a driving fluid, e.g., gas, water, brine, steam, polymer solution, foam, or micellar solution. Ideally, such techniques (commonly called flooding techniques) provide a bank of oil of substantial depth being driven into a producing well; however, in practice this is frequently not the case. Oil-bearing strata are usually heterogeneous, some parts of them being more permeable than others. As a consequence, channeling frequently occurs, so that the driving fluid flows preferentially through permeable zones depleted of oil (so-called "thief zones") rather than through those parts of the strata which contain sufficient oil to make oil-recovery operations profitable.

Difficulties in oil recovery due to thief zones may be corrected by injecting an aqueous solution of an organic polymer and a cross-linking agent into a subterranean formation under conditions where the polymer will be cross-linked to produce a gel, thus reducing permeability of the subterranean formation to driving fluid (gas, water, etc.). Polysaccharide- or partially hydrolyzed polyacrylamide-based fluids cross-linked with certain aluminum, titanium, zirconium, and boron based compounds are used in these enhanced oil recovery applications.

Cross-linked fluids or gels, whether for fracturing a subterranean formation or for reducing permeability of zones in subterranean formation, are now being used in wells under a variety of temperature and pH conditions, where rates of cross-linking with known cross-linking compositions may be unacceptable.

U.S. Pat. No. 4,883,605 discloses a water-soluble zirconium chelate formed from a tetraalkyl zirconate and hydroxyethyl-tris-(2-hydroxypropyl)ethylenediamine, and the use of the chelate as a cross-linking agent in hydraulic fracturing fluids and in gels that are used for selectively plugging permeable zones in subterranean formations or for plugging subterranean leaks.

The products of U.S. Pat. No. 4,883,605 are excellent cross-linkers for use in hotter, deeper oil well applications, where a significant delay in rate of cross-linking is required. For moderate temperature formations, however, these products cross-link too slowly (>10 minutes), causing a "sand out" to occur, which is the result of sand depositing at the bottom of the wellbore due to lack of viscosity development before the gel reaches the fracture zone.

A similar chelate, formed from zirconium tetrachloride and tetra-(2-hydroxypropyl)ethylenediamine and neutralized with sodium hydroxide is disclosed in U.S. Pat. No. 2,824,115, Example IV. This compound has been found to form a slurry in water and be unsuitable for use in these applications. In addition, the presence of sodium chloride in this composition would most likely cause syneresis of the cross-linking gels, rendering them less effective.

Commercially available zirconate cross-linkers, such as tetra-triethanolamine zirconate cross-link too fast, causing a significant loss in viscosity due to shear degradation, which can also result in a sand out.

Other zirconium complexes of triethanolamine, such as those disclosed in U.S. Pat. Nos. 4,578,488, 4,683,068, and 4,686,052 can be used as cross-linking agents, however, these complexes also do not cross-link at a desirable rate, especially in the hotter, deeper wells, causing a similar loss in viscosity due to shear degradation.

There is a need for compositions which cross-link at a rate intermediate between zirconium complexes of hydroxyethyl-tris-(2-hydroxypropyl)ethylenediamine and triethanolamine zirconates which can be used successfully in moderate temperature (250-350° F., 121-177° C.) formations.

SUMMARY OF THE INVENTION

The present invention provides a clear, stable, salt-free solution of a complex having a 1:1 molar ratio of zirconium and N,N,N',N'-tetrakis-(2-hydroxypropyl)-ethylene diamine. The zirconium diamine complex can be represented by Formula I and is an effective cross-linking agent or cross-linker for use in oil field applications. Optional additional ligands may be present on the zirconium central atom.

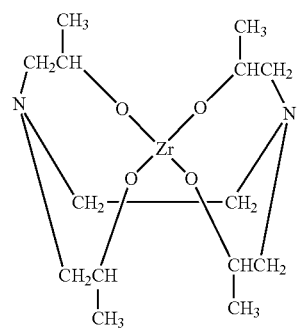

Formula I

The salt-free solution is prepared by a process comprising (a) contacting a solution of a tetraalkyl zirconate with one molar equivalent of N,N,N',N'-tetrakis-(2-hydroxypropyl)-ethylene diamine to produce an initial reaction product; and (b) contacting the initial reaction product with 0.5 to 20 moles of water per mole of zirconium at a temperature in the range of 50° C. to 90° C. for a period of time typically from 2 hours to 10 hours, to produce a clear solution.

There is further provided a cross-linking composition which comprises (a) an aqueous liquid; (b) a pH buffer; (c) a cross-linkable organic polymer; and (d) a salt-free solution comprising a complex having a 1:1 molar ratio of zirconium and N,N,N',N'-tetrakis-(2-hydroxypropyl)-ethylene diamine, water and a solvent.

The cross-linking composition of this invention is useful in oil field applications, for example, for hydraulically fracturing a subterranean formation. The solution of this invention is further useful for plugging permeable zones or leaks in subterranean formations.

This invention provides a method for hydraulically fracturing a subterranean formation which comprises using the salt-free solution of a complex having a 1:1 molar ratio of zirconium and N,N,N',N'-tetrakis-(2-hydroxypropyl)-ethylene diamine. This method comprises introducing (a) an aqueous liquid; (b) a pH buffer; (c) a cross-linkable organic polymer; and (d) a salt-free solution of a complex having a 1:1 molar ratio of zirconium and N,N,N',N'-tetrakis-(2-hydroxypropyl)-ethylene diamine, into a subterranean formation at a flow rate and pressure sufficient to create, reopen and/or extend a fracture in the formation.

This invention provides a method for plugging a permeable zone or leak in a subterranean formation which comprises introducing into said zone or said leak, (a) an aqueous liquid; (b) a pH buffer; (c) a cross-linkable organic polymer; and (d) a salt-free solution of a complex having a 1:1 molar ratio of zirconium and N,N,N',N'-tetrakis-(2-hydroxypropyl)-ethylene diamine.

The present invention provides methods for effective viscosity generation in oil field applications such as fluid fracturing and plugging permeable zones. Surprisingly, the cross-linking composition of this invention cross-links to achieve maximum viscosity in a desirable 5 to 7 minute range at moderate well temperatures, such as 121-177° C. (250-350° F.), whereas similar compositions having zirconium complexes have rates of cross-linking that are too fast or too slow. The cross-linking composition of this invention can tolerate a range of temperature, pH and other conditions.

DETAILED DESCRIPTION OF THE INVENTION

Trademarks and trade names used herein are shown in upper case.

The present invention provides an economical, stable, water-soluble zirconium complex in a salt-free solution. The solution comprises a 1:1 molar complex of zirconium and N,N,N',N'-tetrakis-(2-hydroxypropyl)ethylene diamine, water and a solvent. The zirconium diamine complex can be represented by Formula I.

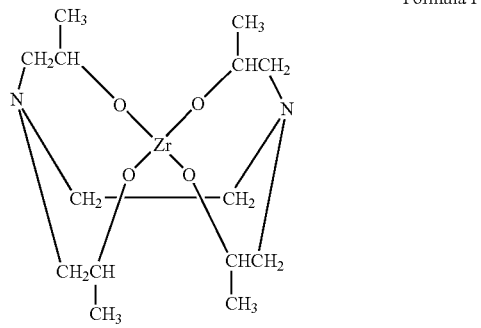

Formula I

Optional additional ligands may be present on the zirconium central atom, including, for example solvent molecules.

The solvent is typically selected form the group consisting of $C_1$-$C_6$ alcohols, preferably $C_3$-$C_4$ alcohols.

The zirconium complex in the solution of this invention is an effective cross-linking agent or cross-linker for use in cross-linking compositions for oil field applications.

The solution of zirconium complex can be prepared by a process which comprises contacting a solution of a tetraalkyl zirconate in a $C_1$-$C_6$ alcohol with one molar equivalent of N,N,N',N'-tetrakis-(2-hydroxypropyl)ethylene diamine (available commercially, for example, from BASF Corporation, Mount Olive, N.J., under the name QUADROL polyol.) to produce an initial reaction product. A number of tetraalkyl zirconates (also known as zirconium tetraalkoxides) can be used to prepare the zirconium complex in the present invention, e.g., tetra-i-propyl zirconate, tetra-n-propyl zirconate, and tetra-n-butyl zirconate. The preferred tetraalkyl zirconate tetra-n-propyl zirconate, available as TYZOR NPZ organic zirconate, a solution in n-propanol, with a zirconium content as $ZrO_2$ of about 28% by weight, available from E. I. du Pont de Nemours and Company, Wilmington, Del. Contacting the zirconate solution with the ethylene diamine derivative can be carried out at a variety of temperatures, e.g., between 25° C. and 92° C., preferably between 50° C. and 80° C.

The initial reaction product of the tetraalkyl zirconate with the diamine is a slurry of the zirconate-diamine complex in the corresponding alkanol (e.g., n-propanol if the alkyl group is n-propyl) from the initial solution of the tetraalkyl zirconate and that which resulted as reaction byproduct. It should be appreciated by those skilled in the art that a slurry of the zirconium complex would be unsuitable for use as a cross-linking agent in hydraulic fracturing fluids and gels because settling occurs and thus inaccurate metering of the zirconium complex in use in an oil field. Dilution of these slurries with an alcohol, such as ethanol or n-propanol, does not result in formation of a stable solution. Surprisingly, contacting the initial reaction product with a small amount of water, typically, 0.5 to 20 moles of water per mole of zirconium at a temperature in the range of 50° C. to 90° C. for a period of time typically from 2 hours to 10 hours, converts the slurry to a clear, stable solution. Preferably, the initial reaction product is contacted with water at a temperature in the range of 60 to 80° C. for a period of time from about 2 to about 4 hours.

Usually contacting an organic zirconium solution with water is avoided because precipitation frequently results, thus, it is surprising in this process that addition of water converts a slurry to a clear solution. The addition of too much water should be avoided because it may lead to precipitation of insoluble zirconium hydroxide polymers over time. The amount of water required may vary somewhat depending on the alkanol content, but is easily determined by a simple experiment by one skilled in the art. Typically the amount of water is between 0.5 moles and 20 moles per mole of zirconium metal, preferably between 1 and 5 moles of water per mole of zirconium metal. Optionally, additional alkanol may be added along with the water as well.

The present invention provides a cross-linking composition which comprises (a) an aqueous liquid; (b) a pH buffer; (c) a cross-linkable organic polymer; and (d) a solution comprising a complex having a 1:1 molar ratio of zirconium and N,N,N',N'-tetrakis-(2-hydroxypropyl)-ethylene diamine and a solvent.

The solution of zirconium complex is the salt-free solution described above. The aqueous liquid is typically selected from the group consisting of water, aqueous alcohol, and aqueous salt solutions. Preferably, the aqueous liquid is water, aqueous methanol, aqueous ethanol, or an aqueous solution of potassium chloride.

The cross-linking composition comprises an effective amount of a pH buffer to control pH. The pH buffer may be acidic, neutral or basic. The pH buffer is generally capable of controlling the pH from about pH 3 to about pH 12. For example, in a composition for use at pH of about 4-5, an acetic acid-based buffer can be used. In a composition for use at a pH of 5-7, a fumaric acid-based buffer or a sodium diacetate-based buffer can be used. In a composition for use at a pH of 7-8.5, a sodium bicarbonate-based buffer can be used. In a composition for use at a pH of 9-12, a sodium carbonate or sodium hydroxide-based buffer can be used. Other suitable pH buffers can be used, as are known to those skilled in the art.

The composition further comprises a cross-linkable organic polymer. Suitable cross-linkable organic polymers are selected from the group consisting of solvatable polysaccharides, polyacrylamides and polymethacrylamides. Preferably the organic polymer is a solvatable polysaccharide and is selected from the group consisting of gums, gum derivatives and cellulose derivatives. Gums include guar gum and locust bean gum, as well as other galactomannan and glucomannan gums, such as those derived from sennas, Brazilwood, tera, honey locust, karaya gum and the like. Gum derivatives include hydroxyethylguar (HEG), hydroxypropylguar (HPG), carboxyethylhydroxyethylguar (CEHEG), carboxymethylhydroxypropylguar (CMHPG), carboxymethyl guar (CMG), and the like. Cellulose derivatives include those containing carboxyl groups, such as carboxymethylcellulose (CMC), carboxymethylhydroxyethylcellulose (CMHEC), and the like. The solvatable polysaccharides can be used individually or in combination; usually, however, a single material is used. Guar derivatives and cellulose derivatives are preferred, such as, HPG, CMC and CMHPG. HPG is generally more preferred based upon its commercial availability and desirable properties. However, CMC and CMHPG may be more preferred in cross-linking compositions when the pH of the composition is less than 6.0 or higher than 9.0, or when the permeability of the formation is such that one wishes to keep the residual solids at a low level to prevent damage to the formation.

The cross-linkable polymer is normally mixed with the aqueous liquid such as water or mixed water/organic solvent or with an aqueous solution to form a base gel. Organic solvents that may be used include alcohols, glycols, polyols, and hydrocarbons such as diesel. As an example, the aqueous liquid is selected from the group consisting of water, a water/alcohol mixture (e.g., where the alcohol is methanol or ethanol), and an aqueous solution comprising a clay stabilizer. Clay stabilizers include, for example, hydrochloric acid and chloride salts, such as, tetramethylammonium chloride (TMAC) or potassium chloride. Aqueous solutions comprising clay stabilizers may comprise, for example, 0.05 to 0.5 weight % of the stabilizer, based on the total weight of the cross-linking composition.

The composition may comprise optional components, including those which are common additives for oil field applications. Thus, the composition may further comprise one or more of proppants, friction reducers, bactericides, hydrocarbons, chemical breakers, stabilizers, surfactants, formation control agents, and the like. Proppants include sand, bauxite, glass beads, nylon pellets, aluminum pellets and similar materials. Friction reducers include polyacrylamides. Hydrocarbons include diesel oil. Chemical breakers break the cross-linked polymer (gel) in a controlled manner and include enzymes, alkali metal persulfate, and ammonium persulfate. Stabilizers include methanol, alkali metal thiosulfate, and ammonium thiosulfate. Stabilizers may also include clay stabilizers such as hydrochloric acid and chloride salts, for example, tetramethylammonium chloride (TMAC) or potassium chloride.

These optional components are added in an effective amount sufficient to achieve the desired cross-linking performance based on the individual components, desired cross-linking time, temperature and other conditions present in the formation being fractured or permeable zone being plugged.

The cross-linking composition is produced by mixing the solution of zirconium complex with the other components, in any order. For example, in one particular application in an oil field, the solution of zirconium complex and optional components are introduced into a formation, while the cross-linkable organic polymer and aqueous liquid are introduced into the formation as a separate stream. Alternatively, all components may be premixed and introduced into a subterranean formation as a single stream. Advantageously, the components may be mixed in different combinations, and more advantageously, the components may be mixed just prior to use to enable easy variation and adjustment of the cross-linking rate.

This invention provides a method for hydraulically fracturing a subterranean formation, which comprises introducing into the formation at a flow rate and pressure sufficient to create, reopen, and/or extend one or more fractures in the formation, a cross-linking composition comprising an aqueous liquid; a pH buffer; a cross-linkable organic polymer; and a solution comprising a complex having a 1:1 molar ratio of zirconium and N,N,N',N'-tetrakis-(2-hydroxypropyl)-ethylene diamine, water and a solvent; and other optional components.

In one embodiment of the method for hydraulically fracturing a subterranean formation, the salt-free solution of zirconium complex and the cross-linkable polymer are contacted prior to their introduction into the formation, such that the cross-linking agent and polymer react to form a cross-linked gel, wherein the gel is introduced into the formation. In this method, a cross-linking composition is prepared by mixing a solution comprising a complex having a 1:1 molar ratio of zirconium and N,N,N',N'-tetrakis-(2-hydroxypropyl)-ethylene diamine, water and a solvent with a base gel. A base gel is prepared by mixing a cross-linkable organic polymer with an aqueous liquid. This method comprises contacting the solution of zirconium complex with the base gel; permitting the zirconium complex and the base gel to react, to form a cross-linked gel; and introducing the cross-linked gel into the formation at a flow rate and pressure sufficient to create, reopen, and/or extend a fracture in the formation. The solution of zirconium complex, the base gel, or both further comprise a pH buffer.

Alternatively, the subterranean formation may be penetrated by a wellbore, such that contacting the solution of zirconium complex with the base gel occurs in the wellbore and the cross-linked gel is introduced into the formation from the wellbore. This method of hydraulically fracturing a subterranean formation penetrated by a wellbore comprises (a) preparing a base gel by mixing a cross-linkable organic polymer with an aqueous liquid; (c) introducing the base gel into the wellbore; (d) simultaneously with or sequentially after, introducing the base gel into the wellbore, introducing a solution comprising a complex having a 1:1 molar ratio of zirconium and N,N,N',N'-tetrakis-(2-hydroxypropyl)-ethylene diamine, water and a solvent, into the wellbore; (e) permitting the base gel and the solution of zirconium complex to react to form a cross-linked aqueous gel; and (e) introducing the cross-linked gel into the formation from the wellbore at a flow rate and pressure sufficient to create, reopen, and/or extend a fracture in the formation. A pH buffer is independently admixed with the base gel, the solution of zirconium complex or both prior to introducing the base gel and the zirconium solution into the wellbore.

Upon creation of a fracture or fractures, the method may further comprise introducing a cross-linking composition comprising the solution of zirconium complex, a cross-linkable organic polymer and proppant into the fracture or fractures. This second introduction of a solution of zirconium complex is preferably performed in the event the cross-linking composition used to create the fracture or fractures did not comprise proppant.

Another use for the solution of zirconium complex of the present invention relates to a method for selectively plugging permeable zones and leaks in subterranean formations which comprises introducing into the permeable zone or the site of the subterranean leak, a cross-linking composition comprising (a) an aqueous liquid; (b) a pH buffer; (c) a cross-linkable organic polymer; and (d) a solution comprising a complex having a 1:1 molar ratio of zirconium and N,N,N',N'-tetrakis-(2-hydroxypropyl)-ethylene diamine, water and a solvent, into the permeable zone or the site of the subterranean leak. The pH buffer may be admixed with the solution of zirconium complex prior to introducing the cross-linking composition into the permeable zone or site of the leak.

In a first embodiment of the method for plugging a permeable zone or a leak in a subterranean formation, the aqueous liquid, pH buffer, cross-linkable organic polymer and the solution of zirconium complex are contacted prior to their introduction into the subterranean formation, such that the polymer and zirconium complex react to form a cross-linked aqueous gel, which gel is then introduced into the formation.

In an alternative embodiment of the method for plugging a permeable zone or a leak in a subterranean formation, the solution of zirconium complex and the cross-linkable organic polymer are introduced separately, either simultaneously or sequentially, into the permeable zone or the site of the subterranean leak such that cross-linking occurs within the subterranean formation. This method comprises (a) preparing a base gel by mixing a cross-linkable organic polymer with an aqueous liquid; (b) introducing the base gel into the into the permeable zone or the site of the subterranean leak; (d) simultaneously with or sequentially after, introducing the base gel into the into the permeable zone or the site of the subterranean leak, introducing the solution of zirconium complex into the into the permeable zone or the site of the subterranean leak; (e) permitting the base gel and the cross-linking agent to react to form a cross-linked aqueous gel to plug the zone and/or leak. The solution of zirconium complex, the base gel, or both further comprise a pH buffer.

The relative amounts of cross-linkable organic polymer and the zirconium complex may vary. One uses small but effective amounts which for both will vary with the conditions, e.g., the type of subterranean formation, the depth at which the method (e.g., fluid fracturing, permeable zone plugging or leak plugging) is to be performed, temperature, pH, etc. Generally one uses as small an amount of each component as will provide the viscosity level necessary to effect the desired result, i.e., fracturing of the subterranean formation, or plugging permeable zones or leaks to the extent necessary to promote adequate recovery of oil or gas from the formation.

For example, satisfactory gels can generally be made for fluid fracturing by using the cross-linkable organic polymer in amounts up to about 1.2 weight % and the cross-linking composition in amounts up to about 0.50 weight % of the zirconium complex, with percentages being based on the total weight. Preferably, from about 0.25 to about 0.75 weight % of the cross-linkable organic polymer is used and from about 0.05 to about 0.25 weight % of the zirconium complex is used.

In a method for plugging permeable zones or leaks, generally about 0.25 to 1.2 weight % of a cross-linkable organic polymer is used, preferably 0.40 to 0.75 weight %, based on the total weight. Generally about 0.01 to 0.50 weight % of the zirconium complex is used, preferably 0.05 to 0.25 weight %, based on the total weight.

The amount of zirconium complex used to cross-link the organic polymer is that which provides a zirconium ion concentration in a range from about 0.0005 weight % to about 0.1 weight %, based on the total weight. The preferred concentration of zirconium ion is in the range of from about 0.001-0.05 weight %, based on the total weight.

Typically the solution of zirconium complex of this invention can be used at a pH of from about 3 to 11. For low temperature applications (150-250° F., 66-121° C.), carbon dioxide-based energized fluids may be used. In this case, a pH for the cross-linking composition of about 3 to about 6 is preferred. For moderate or high temperature applications (250-400° F., 121-204° C.), a pH of about 9 to about 11 is preferred. Advantageously, the solution of zirconium complex of this invention is used at a temperature of 275-325° F. (135-163° C.).

EXAMPLES

The preparation of the compositions in the Examples and in the Controls were each carried out in closed vessels containing an agitator, thermometer, condenser, nitrogen inlet and dropping funnel. Unless specified otherwise, percentages are given by weight. Temperatures are given in degrees Celsius. The cross-linking properties of the compositions of this invention are given in the Examples as a function of the viscosity of carboxymethyl, hydroxypropylguar cross-linked with the zirconate of this invention.

Control 1

Triethanolamine (135.2 g) was added to 100 g of tetra-n-propyl zirconate solution (TYZOR NPZ organic zirconate, available from E. I. du Pont de Nemours and Company, Wilmington, Del.). The reaction mixture was heated to 60° C. and held there for 4 hours. Upon completion of the reaction the resultant solution of tetra(triethanolamine) zirconate was concentrated on a rotary evaporator under reduced pressure to yield 155 g of a viscous yellow oil, which contained 13.2% Zr.

Control 2

Hydroxyethyl tris-2-hydroxypropyl ethylenediamine (146 g) was added to 220.3 g of tetra-n-propyl zirconate. The reaction mixture was heated to 60° C. and held there for 4 hours to give 346 g of a pale yellow liquid containing hydroxyethyl-tris-2-hydroxypropyl ethylenediamine zirconate, containing 12.4% Zr.

Comparative Example A

Zirconium tetrachloride (23.2 g) was dissolved in 200 ml of water and the resulting solution was added to 29.2 g of tetra-2-hydroxypropyl ethylenediamine (QUADROL polyol) in accordance with the process of Example IV of U.S. Pat. No. 2,824,115. The solution was cooled to 25° C. and neutralized to pH 9 with 255 sodium hydroxide solution. Contrary to the results disclosed in U.S. Pat. No. 2,824,115, a white slurry resulted, which could not be used as a cross-linker.

Comparative Example B

A 500 ml flask equipped with an agitator, condenser, nitrogen bubbler and dropping funnel was charged with 220.3 g (0.5 moles) of tetra-n-propyl zirconate. Agitation was started and 74.5 g (0.5 moles) of triethanolamine were added. The mixture was heated to 60° C. and held at this temperature for 2 hours. During the heating period, a white solid separated from the reaction mass. Upon dilution with 9 g (0.5 moles) of water, the solids dissolved. The resultant solution was heated an additional 4 hours at 80° C. to give a 303 g of a pale yellow liquid containing 15% Zr. On standing for several days solids began to precipitate from solution. The combined solution/precipitate of a 1:1 mole ratio of triethanolamine:zirconium could not be used as a cross-linker.

Example 1

Tetra-2-hydroxypropyl ethylenediamine, QUADROL polyol, (66.3 g) was added to 100 g of tetra-n-propyl zirconate (TYZOR NPZ organic zirconate) in a 1:1 mole ratio of the diamine to zirconium. The resultant mixture was heated to 60° C. and held there for 2 hr. During the heating period, a white solid separated from the reaction mass. Upon dilution with 4.1 g of water, the solids dissolved. The resultant solution of zirconium complex of tetra-2-hydroxypropyl ethylenediamine was heated an additional 4 hr at 80° C. to give a 170 g of a pale yellow liquid containing 12.1% Zr.

Example 2

Tetra-2-hydroxypropyl ethylenediamine, QUADROL polyol, (66.3 g) was added to 100 g of tetra-n-propyl zirconate (TYZOR NPZ organic zirconate) in a 1:1 mole ratio of the diamine to zirconium. The resultant mixture was heated to 60° C. and held there for 2 hr. During the heating period, a white solid separated from the reaction mass. Upon dilution with 12.3 g of water, the solids dissolved. The resultant solution of zirconium complex of tetra-2-hydroxypropyl ethylenediamine was heated an additional 4 hr at 80° C. to give a 178 g of a pale yellow liquid containing 11.6% Zr.

Preparation of Base Gel

A Waring blender jar was filled with 1 liter of distilled water. To this was added 2 g of a 50% aqueous solution of tetramethylammonium chloride clay stabilizer. Agitation was started and 3.6 g of carboxymethylhydroxypropylguar (CM-HPG) was sprinkled into the vortex of the agitating solution. The pH of the resultant slurry was adjusted to 6 with sodium diacetate and agitation continued for 30 minutes. The pH was then adjusted to 10.3 with 10% sodium hydroxide solution. Agitation was stopped and the gel was allowed to stand for 30 minutes or more before use.

Viscosity Measurement of Zirconate Cross-Linked Base Gel

To 250 ml of a vigorously agitated sample of base gel in a Waring blender jar, was added 0.00032 moles of zirconium (0.2-1.0 ml dependent on percent zirconium of cross-linker solution—hereinafter referred to as the Standard Loading Density). Agitation was continued for about 15-180 seconds. A 25 ml sample of the cross-linker containing gel was placed in the cup of the FANN 50 Viscometer with an R-1, B-3 configuration and viscosity was measured at 275° F. (135° C.) and 122 rpm at 100 reciprocal seconds of shear.

Table 1 shows the performance of a 30 lb/1000 gallon (3600 g/1000 liters) CMHPG gel cross-linked with both known zirconates (Controls) and those of the invention.

TABLE

| Viscosity of CMHPG Gel with Zirconium Cross-linkers | | | | | | | |
|---|---|---|---|---|---|---|---|
| Sample | % Zr | Loading (ml) | Time to reach maximum Viscosity (min) | Viscosity @ maximum (Cp) | Viscosity after 30 min. @ 275° F., 135° C. (Cp) | Viscosity after 60 min. @ 275° F., 135° C. (Cp) | Viscosity after 90 min. @ 275° F., 135° C. (Cp) |
| Control 1 | 13.2 | 0.18 | 1.5 | 1125 | — | 680 | 660 |
| Control 2 | 12.4 | 0.27 | 12.0 | 300 | 265 | 245 | 225 |
| Example 1 | 12.1 | 0.24 | 7.0 | 650 | 470 | 460 | 445 |
| Example 2 | 11.6 | 0.26 | 6.0 | 670 | 520 | 510 | 500 |

As can be seen from the Table, the zirconium—triethanolamine cross-linking composition in Control 1 generates excellent viscosity; however its rate of cross-linking, as measured by time to reach maximum viscosity, is much too fast at 1.5 minutes. In the field, at this rate of cross-linking, it would be expected that shear degradation and loss of viscosity of the cross-linked gel would occur, prior to reaching the zone to be fractured or plugged in the formation.

As can be seen from the Table, the rate of cross-linking for the hydroxyethyl-tris-2-hydroxypropyl ethylenediamine zirconium complex of Control 2 is very slow. In the field, viscosity generation is so slow at the slow rate of cross-linking, that sand would be expected to drop out of the cross-linking fluid before the fluid reached the zone to be fractured.

As can be seen from the Table, the cross-linking rates containing the solutions of this invention in Examples 1 and 2 are within the desirable range of 3-8 minutes. At these cross-linking rates, the cross-linking compositions can be used in the field for fracturing or plugging, even for hotter, deeper formations. Initial viscosity development with these cross-linkers is somewhat lower, but viscosity retention after 90 minutes is still excellent, which is also favorable for use in hot deep wells.

What is claimed is:

1. A clear, stable, salt-free solution comprising a complex having a 1:1 molar ratio of zirconium and N,N,N',N'-tetrakis-(2-hydroxypropy1)-ethylene diamine, water and a solvent, wherein 0.5 to 20 moles of water per mole of zirconium is added and the solvent is selected from the group consisting of $C_1$-$C_6$ alcohols.

2. The solution of claim 1 wherein the solvent is n-propanol.

3. A process to prepare a clear, stable, salt-free solution comprising (a) contacting a solution of a tetraalkyl zirconate in a $C_1$-$C_6$ alcohol with one molar equivalent of N,N,N',N'-tetrakis-(2-hydroxypropy1)-ethylene diamine to produce an initial solid reaction product, which is a slurry of zirconate-diamine; and (b) contacting the initial reaction product with 0.5 to 20 moles of water per mole of zirconium at a temperature in the range of 25° C. to 92° C. to produce a clear solution.

4. The process of claim 3 wherein step (a) is carried out at a temperature between 50° C. and 90° C.

5. The process of claim 3 wherein step (b) is carried out at a temperature in the range of 60° C. to 80° C.

6. The process of claim 4 wherein the amount of water added is between 1 and 5 moles of water per mole of zirconium.

7. A cross-linking composition comprising (a) an aqueous liquid; (b) a pH buffer; (c) a cross-linkable organic polymer; and (d) a solution comprising a complex having a 1:1 molar ratio of zirconium and N,N,N',N'-tetrakis-(2-hydroxypropyl)-ethylene diamine, water and a solvent wherein 0.5 to 20 moles of water per mole of zirconium is added and the solvent is selected from the group consisting of $C_1$-$C_6$ alcohols.

8. The cross-linking composition of claim 7 wherein the cross-linkable organic polymer is selected from the group consisting of solvatable polysaccharides, polyacrylamides and polymethacrylamides.

9. The cross-linking composition of claim 8 wherein the cross-linkable organic polymer is a solvatable polysaccharide.

10. The cross-linking composition of claim 8 wherein the cross-linkable organic polymer is selected from the group consisting of gums, gum derivatives and cellulose derivatives.

11. The cross-linking composition of claim 8 wherein the cross-linkable organic polymer is hydroxypropylguar, carboxymethylhydroxypropylguar, or carboxymethylcellulose.

12. The cross-linking composition of claim 7 wherein the cross-linkable polymer is mixed with an aqueous liquid.

13. The cross-linking composition of claim 12 wherein the aqueous liquid is an aqueous solution comprising a clay stabilizer.

14. The cross-linking composition of claim 13 wherein the clay stabilizer is hydrochloric acid, tetramethylammonium chloride or potassium chloride.

15. A method for hydraulically fracturing a subterranean formation comprising introducing into a subterranean formation at a flow rate and pressure sufficient to create, reopen and/or extend a fracture in the formation, (a) an aqueous liquid; (b) a pH buffer; (c) a cross-linkable organic polymer; and (d) a solution comprising a complex having a complex having a 1:1 molar ratio of zirconium and N,N,N',N'-tetrakis-(2-hydroxypropyl)-ethylene diamine, water and a solvent, wherein 0.5 to 20 moles of water per mole of zirconium is added and the solvent is selected from the group consisting of C1-C6 alcohols.

16. The method of claim 15 wherein the aqueous liquid, pH buffer, cross-linkable organic polymer; and solution of zirconium complex are contacted prior to their introduction into the subterranean formation.

17. The method of claim 15 wherein the subterranean formation is penetrated by a wellbore and contacting of the solution of zirconium complex (d) with the aqueous liquid (a) and the cross-linkable organic polymer (c) occurs in the wellbore.

18. The method of claim 15 further comprising introducing (e) proppant into the subterranean formation.

19. A method for plugging a permeable zone or leak in a subterranean formation comprising introducing into said zone or said leak, (a) an aqueous liquid; (b) a pH buffer; (c) a cross-linkable organic polymer; and (d) a solution comprising a complex having a 1:1 molar ratio of zirconium and N,N,N',N'-tetrakis-(2-hydroxypropyl)-ethylene diamine, water and a solvent, wherein 0.5 to 20 moles of water per mole of zirconium is added and the solvent is selected from the group consisting of C1-C6 alcohols.

20. The method of claim 19 wherein the aqueous liquid, pH buffer, cross-linkable organic polymer; and solution of zirconium complex are contacted prior to their introduction into the subterranean formation.

21. The method of claim 19 wherein the subterranean formation is penetrated by a wellbore and contacting of the solution of zirconium complex (d) with the aqueous liquid (a) and the cross-linkable organic polymer (c) occurs in the wellbore.

* * * * *